(12) United States Patent
Small et al.

(10) Patent No.: US 7,393,552 B2
(45) Date of Patent: Jul. 1, 2008

(54) COMPOSITIONS COMPRISING PROTEIN AND FATTY ACID

(75) Inventors: Leonard Edwin Small, Cincinnnati, OH (US); Haile Mehansho, Fairfield, OH (US); Shalayna Antoinette Woodly, Cincinnati, OH (US); Raul Victorino Nunes, Loveland, OH (US); Roger William Krummen, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 433 days.

(21) Appl. No.: 10/357,636

(22) Filed: Feb. 4, 2003

(65) Prior Publication Data

US 2003/0203005 A1 Oct. 30, 2003

Related U.S. Application Data

(60) Provisional application No. 60/376,060, filed on Apr. 24, 2002.

(51) Int. Cl.
*A23J 1/00* (2006.01)

(52) U.S. Cl. .................. 426/656; 426/601; 426/602; 426/590; 426/580

(58) Field of Classification Search ................. 426/656, 426/601, 602, 590, 580
See application file for complete search history.

(56) References Cited

U.S. PATENT DOCUMENTS

| | | | |
|---|---|---|---|
| 4,338,346 A | 7/1982 | Brand | |
| 4,399,163 A | 8/1983 | Brennan et al. | |
| 4,411,925 A | 10/1983 | Brennan et al. | |
| 4,423,029 A | 12/1983 | Rizzi | |
| 4,599,152 A | 7/1986 | Ashmead | |
| 4,737,375 A | 4/1988 | Nakel et al. | |
| 4,786,510 A | 11/1988 | Nakel et al. | |
| 4,786,518 A | 11/1988 | Nakel et al. | |
| 4,830,716 A | 5/1989 | Ashmead | |
| 4,863,898 A | 9/1989 | Ashmead et al. | |
| 4,994,283 A | 2/1991 | Mehansho et al. | |
| 5,032,411 A * | 7/1991 | Stray-Gundersen | 426/74 |
| 5,108,761 A | 4/1992 | Andon et al. | |
| 5,118,513 A | 6/1992 | Mehansho et al. | |
| 5,128,374 A | 7/1992 | Kochanowski | |
| 5,151,274 A | 9/1992 | Saltman et al. | |
| 5,186,965 A | 2/1993 | Fox et al. | |
| 5,215,769 A | 6/1993 | Fox et al. | |
| 5,225,221 A | 7/1993 | Camden et al. | |
| 5,232,709 A | 8/1993 | Saltman et al. | |
| 5,314,919 A | 5/1994 | Jacobs | |
| 5,389,387 A | 2/1995 | Zuniga et al. | |
| 5,401,524 A | 3/1995 | Burkes et al. | |
| 5,413,804 A * | 5/1995 | Rhodes | 426/583 |
| 5,422,128 A | 6/1995 | Burkes et al. | |
| 5,424,082 A | 6/1995 | Dake et al. | |
| 5,445,837 A | 8/1995 | Burkes et al. | |
| 5,468,506 A | 11/1995 | Andon | |
| 5,474,793 A | 12/1995 | Meyer et al. | |
| 5,543,163 A | 8/1996 | Groves | |
| 5,547,927 A * | 8/1996 | Cope et al. | 514/2 |
| 5,571,441 A | 11/1996 | Andon et al. | |
| 5,612,026 A | 3/1997 | Diehl | |
| 5,670,344 A | 9/1997 | Mehansho et al. | |
| 5,888,563 A | 3/1999 | Mehansho et al. | |
| 6,436,464 B1 * | 8/2002 | Euber | 426/654 |

FOREIGN PATENT DOCUMENTS

| | | |
|---|---|---|
| EP | 0168112 A2 | 1/1986 |
| WO | WO 99/30576 | 6/1999 |
| WO | WO 02/00042 | 1/2002 |

\* cited by examiner

*Primary Examiner*—Anthony Weier
(74) *Attorney, Agent, or Firm*—Kristin Kohler; Cynthia L. Clay; Kelly L. McDow

(57) ABSTRACT

Described herein are compositions comprising defined protein and lipid components. In particular, the compositions comprise:
  (a) a protein component including a protein selected from whey, casein, and mixtures thereof; and
  (b) a lipid component including a fatty acid material selected from fatty acids, non-glyceryl esters thereof, and mixtures thereof, wherein the lipid component has a median particle size of less than about 1 micron.

8 Claims, No Drawings

COMPOSITIONS COMPRISING PROTEIN AND FATTY ACID

CROSS REFERENCE TO PRIORITY APPLICATION

This application claims priority under Title 35, United States Code 119(e) from Provisional Application Ser. No. 60/376,060, filed Apr. 24, 2002.

FIELD OF THE INVENTION

The present invention relates to compositions comprising protein and fatty acid. The compositions are particularly useful as food or beverage compositions.

BACKGROUND OF THE INVENTION

The use of fatty acids, particularly in orally administered compositions, is beneficial for a variety of health concerns. For example, WO 02/00042, Jandacek et al., published Jan. 3, 2002, describes the use of fatty acids for body weight management. The described approach to body weight management includes orally administered compositions containing a fatty acid, which induces satiety in mammals, thereby reducing food consumption. Other uses of fatty acids have been recently promoted, including the use of omega-3-fatty acids in various compositions for the improvement in, for example, cardiac and skin health.

Unfortunately, however, the formulation of such fatty acids in compositions that are acceptable to consumers is not a trivial matter. Fatty acids are susceptible to instability, including degradation, resulting in rancidity. Moreover, compositions containing fatty acids may be physically unstable, resulting in undesirable separation of various ingredients in the composition. Such instability not only affects the flavor profile of the fatty acid, but can affect the deliverable health benefit as well. Moreover, even wherein the fatty acid remains stable, the fatty acid is often undesirable from a flavor perspective. An example of this undesirability includes omega-3-fatty acids, which can exhibit a fishy off-flavor. It would therefore be desirable to provide compositions that alleviate the problems associated with fatty acid instability and/or undesirable flavor profile.

Certain components are known to provide some level of flavor masking in orally administered compositions. For example, inclusion of strong flavors can mask undesirable flavors to a limited extent. However, these strong flavors are often by themselves undesirable, depending upon consumer preference or the type of composition that is desired, and may not alleviate issues associated with instability.

The present inventors have discovered that compositions comprising a defined protein component and a lipid component containing a fatty acid may be optimized wherein the particle size of the lipid component is within a defined range, as described herein. Indeed, the inventors have discovered that stability may be maximized by providing the lipid component in this defined range. Moreover, the inventors have discovered certain processes which are important for providing a stable composition containing the protein and lipid components. For example, various parameters, including shear conditions and order of addition are important. Accordingly, the inventors have discovered stable compositions containing protein and fatty acid, as well as processes of their preparation. These and other benefits of the present invention are described herein.

SUMMARY OF THE INVENTION

The present invention relates to compositions comprising defined protein and lipid components. In particular, the compositions comprise:
(a) a protein component comprising a protein selected from the group consisting of whey, casein, and mixtures thereof; and
(b) a lipid component comprising a fatty acid material selected from the group consisting of fatty acids, non-glyceryl esters thereof, and mixtures thereof, wherein the lipid component has a median particle size of less than about 1 micron.

The compositions of the present invention are particularly useful as food or beverage compositions.

The present further relates to processes for preparing compositions comprising the protein component and lipid component. The processes are useful for preparing a composition comprising:
(a) a protein component comprising a protein selected from the group consisting of whey, casein, and mixtures thereof; and
(b) a lipid component comprising a fatty acid material selected from the group consisting of fatty acids, non-glyceryl esters thereof, and mixtures thereof;

wherein the process comprises:
(a) combining the protein component with the lipid component to form a protein/lipid mixture;
(b) subjecting the protein/lipid mixture to a condition selected from the group consisting of:
(i) subjecting the protein/lipid mixture to high shear conditions, wherein the high shear conditions are a NP/M of from about 4 Watt/Kg to about 70 Watt/Kg;
(ii) homogenizing the protein/lipid mixture at a pressure of from about 1,000 psi to about 15,000 psi to form a homogenized protein/lipid mixture; and
(iii) combinations thereof.

DETAILED DESCRIPTION OF THE INVENTION

Various documents including, for example, publications and patents, are recited throughout this disclosure. All such documents are hereby incorporated by reference. The citation of any given document is not to be construed as an admission that it is prior art with respect to the present invention.

All percentages and ratios are calculated by weight unless otherwise indicated. All percentages and ratios are calculated based on the total composition unless otherwise indicated.

Referenced herein are trade names for components including various ingredients utilized in the present invention. The inventors herein do not intend to be limited by materials under a certain trade name. Equivalent materials (e.g., those obtained from a different source under a different name or reference number) to those referenced by trade name may be substituted and utilized in the descriptions herein.

In the description of the invention various embodiments or individual features are disclosed. As will be apparent to the ordinarily skilled practitioner, all combinations of such embodiments and features are possible and can result in preferred executions of the present invention.

The compositions herein may comprise, consist essentially of, or consist of any of the elements as described herein.

While various embodiments and individual features of the present invention have been illustrated and described, various other changes and modifications can be made without departing from the spirit and scope of the invention. As will be also be apparent, all combinations of the embodiments and features taught in the foregoing disclosure are possible and can result in preferred executions of the invention.

Definitions

As used herein, the term "NP/M" means net-power-per-unit-mass.

As used herein, the term "Watt/Kg" means watts per kilogram.

As used herein, all median particle sizes are defined in terms of Number Distribution. Number Distribution can be measured using a laser scattering system, e.g., a HORIBA LA910 Particle Size Analyzer (commercially available from Horiba, Calif.).

The Compositions of the Present Invention

The present compositions are useful for a variety of purposes, particularly as foods or beverages, and most preferably beverages. In particular, the present compositions are surprisingly stable and organoleptically appealing, despite the presence of the fatty acid material. The present compositions include those comprising:

(a) a protein component comprising a protein selected from the group consisting of whey, casein, and mixtures thereof; and (b) a lipid component comprising a fatty acid material selected from the group consisting of fatty acids, non-glyceryl esters thereof, and mixtures thereof, wherein the lipid component has a median particle size of less than about 1 micron.

The various components of the present compositions are described further as follows:

The Protein Component

The protein component used herein comprises a protein selected from whey, casein, and mixtures thereof. The protein component may be the protein itself, for example as sodium or calcium caseinate, or may be a component comprising the protein and one or more other materials. For example, various milk proteins are known to one of ordinary skill in the art and may be utilized as the protein component herein.

Wherein the protein component is delivered as the protein itself, casein is the preferred protein for use herein. However, whey or mixtures of casein and whey may also be included. Casein may be utilized as a variety of forms including, for example, sodium or calcium caseinate. Mixtures of sodium and calcium caseinate are preferred for use herein.

Milk proteins include mammalian or vegetable milks such as, for example, whole milk, skim milk, condensed milk, dry milk powder, milk protein concentrate, milk protein isolate, milk protein hydrosylate, and mixtures thereof. To illustrate, milk protein concentrate is prepared via milk ultrafiltration or other means such that the lactose or salt content is reduced, thereby enhancing the protein content. In dry and condensed milk, water is removed but all other components of milk are substantially maintained. All forms of milk protein can comprise, for example, intact milk protein, milk protein hydrosylate, or any combination thereof.

The amount of protein component in the present compositions will depend upon a variety of factors including, for example, whether the protein component is the protein itself or delivered as a milk protein, the amount of protein desired in the final composition, and the like. Preferably, the compositions comprise at least about 0.5% protein, by weight of the composition. More preferably, the compositions comprise from about 0.5% to about 10% protein, even more preferably from about 0.5% to about 8% protein, and most preferably from about 0.5% to about 5% protein, all by weight of the composition. Wherein the protein of the protein component is delivered via milk protein or another component, the amounts may be appropriately adjusted. For example, wherein the protein component is whole or skim milk, the compositions preferably comprise from about 5% to about 75%, more preferably from about 5% to about 40%, and most preferably from about 5% to about 15% of the protein component, all by weight of the composition. As another example, wherein the protein component is dry milk, the compositions preferably comprise from about 0.5% to about 10%, more preferably from about 0.5% to about 8%, and most preferably from about 0.5% to about 5% of the protein component, all by weight of the composition.

The Lipid Component

The lipid component comprises a fatty acid material and, where present, includes any fats or other glycerides present in the composition. The fatty acid material utilized in the present invention is selected from fatty acids, non-glyceryl esters thereof, and mixtures thereof. As used herein, the fatty acid material contains a fatty acid chain, or wherein the fatty acid material is a fatty acid ester, contains a fatty acid chain and an ester chain. Thus, wherein the fatty acid material is a fatty acid, the material is depicted as follows:

wherein "R" is the fatty acid chain which is a saturated or unsaturated chain having at least about 9 carbon atoms, typically from about 9 to about 25 carbon atoms, and wherein "COOH" is a carboxylic acid moiety. More preferably, "R" is a saturated or unsaturated chain having from about 11 to about 23, preferably from about 15 to about 21 carbon atoms and, depending upon the embodiment herein, often preferably from about 15 to about 17 carbon atoms. Also preferably, the fatty acid chain contains from 0 to about 3 double bonds. Most preferably, the fatty acid chain is unsaturated, in particular having one or two double bonds.

Wherein the fatty acid material is a non-glyceryl ester of a fatty acid (i.e., a "non-glyceryl ester thereof"), the material is depicted as follows:

Wherein R is the fatty acid chain as defined above, and R' is the ester chain, with the carboxylate moiety "COO" linking the two together. The ester chain is a straight or branched chain of carbon atoms which is hydrolyzable in the presence of mammalian digestive enzymes, preferably human digestive enzymes, and typically contains no more than about 8 carbon atoms. The ester chain more preferably contains from 1 to about 5 carbon atoms and, again, may be a straight (for example, n-propyl) or branched (for example, which form methyl esters (i.e., R' is —CH$_3$), ethyl esters, n-propyl esters, iso-propyl esters, n-butyl esters, iso-butyl esters, and mixtures thereof. Those ester chains which form ethyl esters are particularly preferred.

In a preferred embodiment of the present invention, the fatty acid material is selected from lauric acid, lauroleic acid, myristic acid, myristoleic acid, pentadecanoic acid, palmitic acid, palmitoleic acid, margaric acid, stearic acid, dihydroxystearic acid, oleic acid, ricinoleic acid, elaidic acid, linoleic acid, alpha-linolenic acid, dihomogamma-linolenic acid, eleostearic acid, licanic acid, arachidonic acid, arachidic acid, eicosenoic acid, eicosapentaenoic acid, behenic acid, erucic acid, docosahexaenoic acid, lignoceric acid, non-glyceryl esters thereof, and mixtures thereof. Preferred non-glyceryl esters of fatty acids include ethyl oleate, ethyl linoleate, and mixtures thereof.

In a particularly preferred embodiment of the present invention, the fatty acid material is selected from lauric acid, lauroleic acid, myristic acid, myristoleic acid, pentadecanoic acid, palmitic acid, palmitoleic acid, margaric acid, stearic acid, dihydroxystearic acid, oleic acid, ricinoleic acid, elaidic acid, linoleic acid, alpha-linolenic acid, dihomogamma-linolenic acid, eleostearic acid, licanic acid, arachidonic acid, arachidic acid, eicosenoic acid, behenic acid, erucic acid, lignoceric acid, non-glyceryl esters thereof, and mixtures thereof. In this embodiment of the invention, it is particularly preferred to select a fatty acid material containing from 0 to about 3 double bonds and having a fatty acid chain length of from about 15 to about 17 carbon atoms. Additionally, particularly preferred fatty acid materials include oleic acid, linoleic acid, non-glyceryl esters thereof, and mixtures thereof. Preferred esters of this embodiment include ethyl oleate, ethyl linoleate, and mixtures thereof. As an example, ethyl oleate may be obtained from a variety of sources, including Victorian Chemical Co., Richmond, Victoria; Penta Manufacturing Co., Livingston, N.J.; and Croda, Inc., Parsippany, N.J.

In another preferred embodiment of the present invention, the fatty acid material is selected from omega-3-fatty acids, non-glyceryl esters thereof, and mixtures thereof. The omega-3-fatty acids are particularly preferred for use herein due to their beneficial effects on the health of the consumer, particularly in the fields of skin and cardiac health.

As is well-understood in the art, and as consistently used herein, the term "omega-3-fatty acid" is utilized to refer to those fatty acid materials having an omega-3 double bond wherein the omega-3 double bond is positioned between the third and fourth carbon atoms of the fatty acid chain when counting from the omega (distal) carbon atom of the chain. Omega-3-fatty acids are preferably derived from marine (fish) sources, including menhaden (a herring-like fish). Non-limiting examples of preferred omega-3-fatty acid sources include OMEGAPURE, commercially available from Omega Protein, Inc., Houston, Tex.

Non-limiting examples of omega-3-fatty acids which are suitable for use herein include eicosapentaenoic acid (also known as EPA), docosahexaenoic acid (also known as DHA), and mixtures thereof. Non-glyceryl esters thereof are also contemplated.

In a typical embodiment of the present invention, the compositions comprise from about 0.0001% to about 10% of the fatty acid material, by weight of the composition, and depending upon the particular embodiment desired (for example, a concentrate suitable for further dilution or a ready-to-drink beverage composition). More preferably the comprise from about 0.01% to about 5% of the fatty acid material, by weight of the composition. Even more preferably, the compositions comprise from about 0.01% to about 3% of the fatty acid material, by weight of the composition. Most preferably, the compositions comprise from about 0.5% to about 2.5% of the fatty acid material, by weight of the composition. For example, a typical composition of the present invention may comprise from about 1% to about 1.3% of the fatty acid material, by weight of the composition.

Particle Size of the Lipid Component

In certain embodiments herein, the lipid component has a median particle size of less than about 1 micron. In a particularly preferred embodiment, the lipid component has a median particle size of from about 0.3 microns to about 0.9 microns, most preferably from about 0.4 microns to about 0.8 microns. Indeed, the present inventors have discovered that these particle sizes can be important for the successful emulsification of the lipid component in the milk protein. As discovered, compositions having this lipid component particle size are physically stable and organoleptically acceptable, despite the presence of the lipid component in combination with the protein component.

Further Embodiments of the Present Compositions

The present inventors have further discovered compositions that comprise the protein and lipid components, as well a mineral. Accordingly, in a further embodiment of the present invention, the present compositions comprise one or more minerals selected from the group consisting of iron, calcium, zinc, copper, magnesium, manganese, and mixtures thereof. Preferably, the mineral is a is a divalent salt having the formula:

MA wherein M is a divalent metal selected from the group consisting of iron, calcium, zinc, copper, magnesium, manganese, and mixtures thereof, and wherein A is a dicarboxylate anion. Typical dicarboxylate anions include, for example, succinate, malonate, glutarate, adipate, fumarate, and maleate. Representative divalent mineral salts include, for example, ferrous succinate, ferrous fumarate, calcium succinate, calcium fumarate, zinc succinate, zinc fumarate, cuprous succinate, cuprous fumarate, magnesium succinate, magnesium fumarate, manganese succinate, manganese fumarate, and mixtures thereof. Particularly preferred salts include ferrous fumarate, ferrous succinate, and mixtures thereof.

Wherein a given mineral is present in the composition, the composition preferably comprises at least about 1%, preferably at least about 5%, more preferably from about 10% to about 100%, even more preferably from about 10% to about 70%, and most preferably from about 10% to about 50% of the USRDI of such mineral. The U.S. Recommended Daily Intake (USRDI) for vitamins and minerals are defined and set forth in the Recommended Daily Dietary Allowance-Food and Nutrition Board, National Academy of Sciences-National Research Council.

In an even more preferred embodiment, the inventors have discovered that one or more emulsified minerals, such as those described in Mehansho et al., U.S. Pat. No. 5,888,563, issued Mar. 30, 1999, do not interfere with the foregoing lipid component emulsified in the protein component. Moreover, the present inventors have discovered that the emulsified mineral is stable with such emulsified lipid component, and promotes a desirable flavor profile despite the presence of the mineral and lipid component, which are known exhibit unpleasant flavors. Importantly, it has been found that the emulsified minerals can be characterized as vesicle components, wherein the vesicle components can be processed during preparation of the composition without being disrupted or compromised when combined with the protein component and lipid component mixture.

Accordingly, preferred compositions herein comprise an emulsifier. As defined herein, the emulsifier is additional to the lipid component and the protein component. The preferred minerals herein can be emulsified in accordance with Mehansho et al., U.S. Pat. No. 5,888,563, issued Mar. 30, 1999. For example, suitable emulsifiers include those selected from phospholipids, glycolipids, and mixtures thereof. Among these, more preferred emulsifiers include those selected from lecithins, cephalins, plasmalogens, and mixtures thereof. The most preferred emulsifier for use herein is lecithin. Lecithin may be commercially obtained, for example, as soy lecithin (commercially available from Central Soya, Fort Wayne, Ind.). Preferably, wherein the compositions comprise an emulsifier, the compositions comprise from about 0.01% to about 1%, more preferably from about 0.01% to about 0.5%, and most preferably from about 0.02% to about 0.04% of the emulsifier, all by weight of the composition.

As described in Mehansho et al., the emulsifier may optionally be combined with an edible substrate or bilayer stabilizer, for example, in the amounts specified therein.

Other Optional Components and Uses of the Present Compositions

The compositions described herein are useful in a wide variety of finished compositions, including food or beverage compositions, particularly beverage compositions. Such food and beverage compositions include not only "traditional" foods and beverages, but also those such as dietary supplements and medical foods, and the like, under regulatory guidelines.

The compositions of the present invention may comprise one or more additional optional components to, for example, enhance their performance or to otherwise render the composition more suitable for use as an industrial or consumer product. Accordingly, the present processes may optionally involve inclusion of one or more of these optional components. These components may be added to the compositions herein provided they do not substantially hinder important properties, particularly stabilization or organoleptic properties, of the compositions. Non-limiting examples of optional components are given below:

Water

Water is typically included in the compositions of the present invention, particularly wherein the compositions are beverage compositions. As used herein, the term "water" includes the total amount of water present in the composition including from, for example, fluid milk or other milk protein source, fruit juice, or vegetable juice, as well as any added water. Water is preferably included at levels from about 10% to about 99.999%, more preferably from about 5% to about 99%, still more preferably at least about 50%, even more preferably at least about 70%, and most preferably from about 70% to about 99%, by weight of the composition. Ready-to-drink beverage compositions will typically comprise at least about 70% water, preferably from about 75% to about 99% water, all by weight of the composition. Ready-to-drink beverage compositions are particularly preferred.

Flavor Agents

The compositions herein may optionally, but preferably, comprise one or more flavor agents. Preferably, such flavor agents are included in the beverage compositions and are typically selected from fruit juice, fruit flavors, botanical flavors, and mixtures thereof. Wherein fruit juice is included, the beverages of the present invention can comprise from about 0.1% to about 99%, preferably from about 1% to about 50%, more preferably from about 2% to about 30%, and most preferably from about 5% to about 20%, fruit juice. As measured herein, the weight percentage of fruit juice is based on a single strength 2° to 16° Brix fruit juice. The fruit juice can be incorporated into the beverage as a puree, comminute, or as a single strength or concentrated juice. Especially preferred is incorporation of the fruit juice as a concentrate with a solids content (primarily as sugar solids) of from about 20° to about 80° Brix.

The fruit juice can be any citrus juice, non-citrus juice, or mixture thereof, which are known for use in dilute juice beverages. The juice can be derived from, for example, apple, cranberry, pear, peach, plum, apricot, nectarine, grape, cherry, currant, raspberry, gooseberry, elderberry, blackberry, blueberry, strawberry, lemon, lime, mandarin, orange, grapefruit, cupuacu, potato, tomato, lettuce, celery, spinach, cabbage, watercress, dandelion, rhubarb, carrot, beet, cucumber, pineapple, coconut, pomegranate, kiwi, mango, papaya, banana, watermelon, passion fruit, tangerine, and cantaloupe. Preferred juices are derived from apple, pear, lemon, lime, mandarin, grapefruit, cranberry, orange, strawberry, tangerine, grape, kiwi, pineapple, passion fruit, mango, guava, raspberry and cherry. Citrus juices, preferably grapefruit, orange, lemon, lime, and mandarin juices, as well as juices derived from mango, apple, passion fruit, and guava, as well as mixtures of these juices are most preferred.

Fruit flavors may also be utilized, including flavors which mimic or are derived from any of the fruits described above. As described above with respect to flavor emulsions, fruit flavors may be derived from natural sources such as essential oil and extracts, or can be synthetically prepared. Fruit flavors may be derived from fruits through processing, particularly concentration. Wherein fruit juices are concentrated or evaporated, the condensate contains volatile substances that comprise the flavor of the fruit. Often, such flavor is added to a juice concentrate to enhance the flavor thereof.

Botanical flavors may also be utilized. As used herein, the term "botanical flavor" refers to a flavor derived from parts of a plant other than the fruit; i.e., derived from nuts, bark, roots, and/or leaves. Also included within the term "botanical flavor" are synthetically prepared flavors made to simulate botanical flavors derived from natural sources. Botanical flavors can be derived from natural sources such as essential oils and extracts, or can be synthetically prepared. Suitable botanical flavors include tea, coffee, chocolate, vanilla, jamaica, kola, marigold, chrysanthemum, chamomile, ginger, valerian, yohimbe, hops, eriodictyon, ginseng, bilberry, rice, red wine, mango, peony, lemon balm, nut gall, oak chip, lavender, walnut, gentiam, luo han guo, cinnamon, angelica, aloe, agrimony, yarrow and mixtures thereof. Particularly preferred flavors include chocolate or vanilla.

Wherein coffee solids are included, the compositions typically comprise from about 3% to about 23% coffee solids, by weight of the composition. Wherein tea solids are included, the compositions of the present invention can comprise from about 0.01% to about 1.2%, preferably from about 0.05% to about 0.8%, by weight of the composition, of tea solids. The term "tea solids" as used herein means solids extracted from tea materials including those materials obtained from the genus *Camellia* including *C. sinensis* and *C. assaimica*, for instance, freshly gathered tea leaves, fresh green tea leaves that are dried immediately after gathering, fresh green tea leaves that have been heat treated before drying to inactivate any enzymes present, unfermented tea, instant green tea, and partially fermented tea leaves. Green tea solids are tea leaves, tea plant stems, and other plant materials that are related and which have not undergone substantial fermentation to create black teas. Members of the genus *Phyllanthus, Catechu gambir* and *Uncaria* family of tea plants can also be used. Mixtures of unfermented and partially fermented teas can be used.

Sweeteners

The compositions of the present invention can contain an effective amount of one or more sweeteners, including carbohydrate sweeteners and natural or artificial no/low calorie sweeteners. The amount of the sweetener used in the compositions of the present invention typically depends upon the particular sweetener used and the sweetness intensity desired. For no/low calorie sweeteners, this amount varies depending upon the sweetness intensity of the particular sweetener.

The compositions of the present invention can be sweetened with any of the carbohydrate sweeteners, preferably monosaccharides and/or disaccharides. Sweetened compositions, particularly beverages, will typically comprise from about 0.1% to about 40%, more preferably from about 0.1% to about 20%, and most preferably from about 6% to about 14%, sweetener, all by weight of the composition. These sweeteners can be incorporated into the compositions in solid or liquid form but are typically, and preferably, incorporated as a syrup, most preferably as a concentrated syrup such as high fructose corn syrup. For purposes of preparing beverages of the present invention, these sugar sweeteners can be provided to some extent by other components of the beverage such as, for example, the fruit juice component and/or flavors.

Preferred sugar sweeteners for use in compositions of the present invention are sucrose, fructose, glucose, and mixtures thereof. Fructose can be obtained or provided as liquid fructose, high fructose corn syrup, dry fructose or fructose syrup. High fructose corn syrup (HFCS) is commercially available as HFCS42, HFCS-55 and HFCS-90, which comprise 42%, 55% and 90%, respectively, by weight of the sugar solids therein, as fructose. Other naturally occurring sweeteners or their purified extracts, such as glycyrrhizin, the protein sweetener thaumatin, the juice of Luo Han Guo disclosed in, for example, Fischer et al., U.S. Pat. No. 5,433,965, issued Jul. 18, 1995, and the like can also be used in the compositions of the present invention.

Suitable no/low calorie sweeteners include, for example, saccharin, cyclamates, L-aspartyl-L-phenylalanine lower alkyl ester sweeteners (e.g., aspartame); L-aspartyl-D-alanine amides disclosed in Brennan et al., U.S. Pat. No. 4,411,925; L-aspartyl-D-serine amides disclosed in Brennan et al., U.S. Pat. No. 4,399,163; L-aspartyl-L-1-hydroxymethylalkaneamide sweeteners disclosed in Brand, U.S. Pat. No. 4,338,346; L-aspartyl-1-hydroxyethylalkaneamide sweeteners disclosed in Rizzi, U.S. Pat. No. 4,423,029; L-aspartyl-D-phenylglycine ester and amide sweeteners disclosed in Janusz, European Patent Application 168,112, published Jan. 15, 1986; N-[N-3,3-dimethylbutyl)-L-alpha-aspartyl]-L-phenylalanine 1-methyl ester sweeteners disclosed in Gerlat et al., WO 99/30576 assigned to The Nutrasweet Co., published Jun. 24, 1999; alltame, thaumatin; dihydrochalcones; cyclamates; steviosides; glycyrrhizins, synthetic alkoxy aromatics; sucralose; suosan; miraculin; monellin; sorbitol, xylitol; talin; cyclohexylsulfamates; substituted imidazolines; synthetic sulfamic acids such as acesulfame, acesulfame-K and n-substituted sulfamic acids; oximes such as perilartine; peptides such as aspartyl malonates and succanilic acids; dipeptides; amino acid based sweeteners such as gem-diaminoalkanes, meta-aminobenzoic acid, L-aminodicarboxylic acid alkanes, and amides of certain alpha-aminodicarboxylic acids and gem-diamines; and 3-hydroxy-4-alkyloxyphenyl aliphatic carboxylates or heterocyclic aromatic carboxylates; erythritol; and mixtures thereof.

Coloring Agent

Coloring agents may be utilized in the compositions of the present invention. For example, natural or artificial colors may be used.

FD&C dyes (e.g., yellow #5, blue #2, red # 40) and/or FD&C lakes are preferably used. By adding the lakes to the other powdered ingredients, all the particles, in particular the colored iron compound, are completely and uniformly colored and a uniformly colored composition is attained. Preferred lake dyes which may be used in the present invention are the FDA-approved Lake, such as Lake red #40, yellow #6, blue #1, and the like. Additionally, a mixture of FD&C dyes or a FD&C lake dye in combination with other conventional food and food colorants may be used.

Other coloring agents, for example, natural agents may be utilized. Non-limiting examples of such other coloring agents include fruit and vegetable juices, riboflavin, carotenoids (for example, beta-carotene), tumeric, and lycopenes.

The exact amount of coloring agent used will vary, depending on the agents used and the intensity desired in the finished composition. Generally, if utilized, the coloring agent is typically present at a level of from about 0.0001% to about 0.5%, preferably from about 0.001% to about 0.1%, and most preferably from about 0.004% to about 0.1%, by weight of the composition.

Nutrients

In addition to, or alternative to, the mineral salts described herein, the present compositions may optionally comprise one or more other nutrients, defined herein as one or more vitamins and/or minerals.

Unless otherwise specified herein, wherein a given mineral is present in the composition, the composition comprises at least about 1%, preferably at least about 5%, more preferably from about 10% to about 100%, even more preferably from about 10% to about 70%, and most preferably from about 10% to about 50% of the USRDI of such mineral. Unless otherwise specified herein, wherein a given vitamin is present in the composition, the composition comprises at least about 1%, preferably at least about 5%, more preferably from about 10% to about 200%, even more preferably from about 20% to about 150%, and most preferably from about 25% to about 120% of the USRDI of such vitamin. The U.S. Recommended Daily Intake (USRDI) for vitamins and minerals are defined and set forth in the Recommended Daily Dietary Allowance-Food and Nutrition Board, National Academy of Sciences-National Research Council.

Commercially available vitamin A sources may also be included in the present compositions. As used herein, "vitamin A" includes, but is not limited to, retinol, β-carotene, retinol palmitate, and retinol acetate. The vitamin A may be in the form of, for example, an oil, beadlets or encapsulated.

Wherein vitamin A is present in the compositions herein, the composition comprises at least about 1%, preferably at least about 5%, more preferably from about 10% to about 200%, even more preferably from about 15% to about 150%, and most preferably from about 20% to about 120% of the USRDI of vitamin A. The quantity of vitamin A to be added is dependent on processing conditions and the amount of vitamin A deliver desired after storage. Preferably, wherein vitamin A is included within the present compositions, the compositions comprise from about 0.0001% to about 0.2%, more preferably from about 0.0002% to about 0.12%, also preferably from about 0.0003% to about 0.1%, even more preferably from about 0.0005% to about 0.08%, and most preferably from about 0.001% to about 0.06% of vitamin A, by weight of the composition.

Commercially available sources of vitamin $B_2$ (also known as riboflavin) may be utilized in the present compositions. Wherein vitamin $B_2$ is present in the compositions herein, the composition comprises at least about 1%, preferably at least about 5%, more preferably from about 5% to about 200%, even more preferably from about 10% to about 100%, and most preferably from about 10% to about 50% of the USRDI of vitamin $B_2$.

Commercially available sources of vitamin C can be used herein. Encapsulated ascorbic acid and edible salts of ascorbic acid can also be used. Wherein vitamin C is present in the compositions herein, the composition comprises at least about 1%, preferably at least about 5%, more preferably from about 10% to about 200%, even more preferably from about 20% to about 150%, and most preferably from about 25% to about 120% of the USRDI of such vitamin.

The quantity of vitamin C to be added is dependent on processing conditions and the amount of vitamin C deliver desired after storage. Preferably, wherein vitamin C is included within the present compositions, the compositions comprise from about 0.005% to about 0.2%, more preferably from about 0.01% to about 0.12%, also preferably from about 0.02% to about 0.1%, even more preferably from about 0.02% to about 0.08%, and most preferably from about 0.03% to about 0.06% of vitamin C, by weight of the composition.

Nutritionally supplemental amounts of other vitamins which may be incorporated herein include, but are not limited to, biotin, vitamins $B_1$, $B_3$, $B_6$ and $B_{12}$, folic acid, pantothenic acid, folic acid, vitamin D, and vitamin E. Wherein the composition comprises one of these vitamins, the composition preferably comprises at least 5%, preferably at least 25%, and most preferably at least 35% of the USRDI for such vitamin.

Non-limiting examples of minerals include iodine, chromium, magnesium, manganese, molybdenum, selenium, phosphorous, magnesium, zinc, iodine, iron, and copper. As an example, any soluble salt of these minerals suitable for inclusion in edible compositions can be used, for example, magnesium citrate, magnesium gluconate, magnesium sulfate, zinc chloride, zinc sulfate, potassium iodide, copper sulfate, copper gluconate, and copper citrate.

Calcium is a particularly preferred mineral for use in the present invention. Preferred sources of calcium include, for example, amino acid chelated calcium, calcium carbonate, calcium oxide, calcium hydroxide, calcium sulfate, calcium chloride, calcium phosphate, calcium hydrogen phosphate, calcium dihydrogen phosphate, calcium citrate, calcium malate, calcium titrate, calcium gluconate, calcium propionate, tricalcium phosphate, and calcium lactate, and in particular calcium citrate-malate.

The form of calcium citrate-malate is described in, e.g., U.S. Pat. Nos. 5,670,344; 5,612,026; 5,571,441; 5,474,793; 5,468,506; 5,445,837; 5,424,082; 5,422,128; 5,401,524; 5,389,387; 5,314,919; 5,232,709; 5,225,221; 5,215,769; 5,186,965; 5,151,274; 5,128,374; 5,118,513; 5,108,761; 4,994,283; 4,786,510; and 4,737,375.

Wherein calcium is included, the compositions will typically comprise from about 0.01% to about 0.5%, more preferably from about 0.03% to about 0.2%, even more preferably from about 0.05% to about 0.15%, and most preferably from about 0.1% to about 0.15% of calcium, all by weight of the composition. This calcium includes all forms of calcium included in the composition, such as the divalent calcium salt specified herein, all other forms of calcium described in this section, and all mixtures thereof.

Iron may be utilized in the compositions of the present invention. Acceptable forms of iron are well-known in the art. The amount of iron compound incorporated into the composition will vary widely depending upon the level of supplementation desired in the final composition and the targeted consumer. Iron fortified compositions of the present invention typically contain from about 5% to about 100%, preferably from about 15% to about 50%, and most preferably about 20% to about 40% of the USRDI for iron.

Highly bioavailable ferrous salts that can be used in the ingestible compositions of the present invention are ferrous sulfate, ferrous fumarate, ferrous succinate, ferrous gluconate, ferrous lactate, ferrous tartarate, ferrous citrate, ferrous amino acid chelates, as well as mixtures of these ferrous salts. While ferrous iron is typically more bioavailable, certain ferric salts can also provide highly bioavailable sources of iron.

Certain ferric salts can also provide highly bioavailable sources of iron. Highly bioavailable ferric salts that can be used in the food or beverage compositions of the present invention are ferric saccharate, ferric ammonium citrate, ferric citrate, ferric sulfate, ferric pyrophosphate, ferric orthophosphate, as well as mixtures of these ferric salts. Combinations or mixtures of highly bioavailable ferrous and ferric salts can be used.

A particularly preferred ferric iron source is ferric pyrophosphate, for example, microencapsulated SUNACTIVE Iron, commercially available from Taiyo International, Inc., Edina, Minn., U.S.A and Yokkaichi, Mie, Japan. SUNACTIVE Iron is particularly preferred for use herein due to its particle size, compatibility, and bioavailability.

Ferrous amino acid chelates particularly suitable as highly bioavailable iron sources for use in the present invention are those having a ligand to metal ratio of at least 2:1. For example, suitable ferrous amino acid chelates having a ligand to metal mole ratio of two are those of formula:

$$Fe(L)_2$$

where L is an alpha amino acid, dipeptide, tripeptide, or quadrapeptide ligand. See e.g., U.S. Pat. Nos. 4,863,898; 4,830,716; and 4,599,152. Particularly preferred ferrous amino acid chelates are those where the reacting ligands are glycine, lysine, and leucine. Most preferred is the ferrous amino acid chelate sold under the mark FERROCHEL (Albion Laboratories, Salt Lake City, Utah) wherein the ligand is glycine.

Other sources of iron particularly suitable for fortifying compositions of the present invention included certain iron-sugar-carboxylate complexes. In these iron-sugar-carboxylate complexes, the carboxylate provides the counterion for the ferrous or ferric iron. These iron-sugar-carboxylate complexes can be prepared in the manner described in, e.g., Nakel et al., U.S. Pat. Nos. 4,786,510 and 4,786,518, issued Nov. 22, 1988. These materials are referred to as "complexes", but they may exist in solution as complicated, highly hydrated, protected colloids; the term "complex" is used for the purpose of simplicity.

Zinc may also be utilized in the compositions of the present invention. Acceptable forms of zinc are well-known in the art. Zinc fortified compositions of the present invention typically contain from about 5% to about 100%, preferably from about 15% to about 50%, and most preferably about 25% to about 45% of the USRDI for zinc. The zinc compounds which can be used in the present invention can be in any of the commonly used forms such as, e.g., zinc sulfate, zinc chloride, zinc acetate, zinc gluconate, zinc ascorbate, zinc citrate, zinc aspartate, zinc picolinate, amino acid chelated zinc, and zinc oxide. Zinc gluconate and amino acid chelated zinc are particularly preferred.

Fiber

Fibers are well-known in the art and include complex carbohydrates resistant to digestion by mammalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and man-made fibers (for example, by bacterial synthesis). Commercial fibers such as purified plant cellulose, or cellulose flour, can also be used. Naturally occurring fibers include fiber from whole citrus peel, citrus albedo, sugar beets, citrus pulp and vesicle solids, apples, apricots, and watermelon rinds.

Particularly preferred fibers for use herein are glucose polymers, preferably those which have branched chains, and which are typically less digestible relative to starches and maltodextrins. Preferred among these fibers is one marketed under the trade name FIBERSOL2, commercially available from Matsutani Chemical Industry Co., Itami City, Hyogo, Japan.

Fructo-oligosaccharides are also preferred fibers herein. The preferred fructo-oligosaccharides are a mixture of fructo-oligosaccharides com linked to a molecule of sucrose. Most preferably, they have a nystose to kestose to fructosyl-nystose ratio of about 40:50:10, by weight of the composition. Preferred fructo-oligosaccharides may be obtained by enzymatic action of fructosyltransferase on sucrose such as those which are, for example, commercially available from Beghin-Meiji Industries, Neuilly-sur-Seine, France.

Other preferred fibers for use herein include arabinogalactans. Non-limiting examples of preferred, commercially available sources of arabinogalactan include LAREX UF, LARACARE A200, IMMUNENHANCER (CAS No. 9036-66-2), CLEARTRAC, FIBERAID, and AC-9, all commercially available from (for example) Larex, Inc. of St. Paul, Minn.

These dietary fibers may be in a crude or purified form. The dietary fiber used may be of a single type (e.g., cellulose), a composite dietary fiber (e.g., citrus albedo fiber containing cellulose and pectin), or some combination of fibers (e.g., cellulose and a gum). The fibers can be processed by methods known to the art.

Wherein a fiber is utilized, the desired total level of fiber for the present compositions of the present invention is typically from about 0.01% to about 15%, preferably from about 0.1% to about 5%, more preferably from about 0.1% to about 3%, and most preferably from about 0.2% to about 2%, all by weight of the composition. The total amount of fiber includes any added fiber as well as any soluble dietary fiber naturally present in any other component of the present invention.

Carbonation Component

Carbon dioxide can be introduced into the water which is mixed with a beverage syrup or into the dilute beverage after dilution to achieve carbonation. The carbonated beverage can be placed into a container, such as a bottle or can, and then sealed. Any conventional carbonation methodology may be utilized to make carbonated beverage compositions of this invention. The amount of carbon dioxide introduced into the beverage will depend upon the particular flavor system utilized and the amount of carbonation desired.

pH

The compositions of the present invention may have various pH levels. For example, the compositions may be acidic in nature (for example a pH of from about 3 to about 5) or more basic. Preferred compositions of the present invention have a pH of from about 6 to about 8, more preferably from about 6.3 to about 7.4.

Organic as well as inorganic edible acids may be used to lower the pH of the beverage composition. The acids can be present in their undissociated form or, alternatively, as their respective salts, for example, potassium or sodium hydrogen phosphate, potassium or sodium dihydrogen phosphate salts. The preferred acids are edible organic acids including citric acid, malic acid, fumaric acid, adipic acid, phosphoric acid, gluconic acid, tartaric acid, ascorbic acid, acetic acid, phosphoric acid or mixtures thereof. The most preferred acids are citric and malic acids. Glucono Delta Lactone (GDL) is also a preferred acid for use herein, particularly wherein it is desired to reduce pH without introducing excessive acidic, or tart, flavor in to the final composition.

For those compositions that are more basic in nature, various bases may be utilized. For example, sodium hydroxide or potassium hydroxide may be used herein.

The Processes of the Present Invention

The present invention further relates to processes for preparing certain compositions. As discovered, these processes are important for emulsification of the lipid component in protein. In particular, the present inventors have discovered that certain high shear conditions and homogenization procedures, as enabled herein, are important for the preparation of physically stable final compositions that exhibit desirable organoleptic properties.

In particular, the present processes comprise preparing a composition comprising:
 (a) a protein component comprising a protein selected from the group consisting of whey, casein, and mixtures thereof; and
 (b) a lipid component comprising a fatty acid material selected from the group consisting of fatty acids, non-glyceryl esters thereof, and mixtures thereof;

wherein the process comprises:
 (a) combining the protein component with the lipid component to form a protein/lipid mixture;
 (b) subjecting the protein/lipid mixture to a condition selected from the group consisting of:
  (i) subjecting the protein/lipid mixture to high shear conditions, wherein the high shear conditions are a NP/M of from about 4 Watt/Kg to about 70 Watt/Kg;
  (ii) homogenizing the protein/lipid mixture at a pressure of from about 1,000 psi to about 15,000 psi to form a homogenized protein/lipid mixture; and
  (iii) combinations thereof.

The protein component and lipid component are described in detail herein above. Preferably, the process results in the lipid component having the median particle size described herein above. The process is described in further detail, as follows:

In another embodiment, the high shear conditions may be a NP/M of from about 10 Watt/Kg to about 50 Watt/Kg, alternatively 10 Watt/Kg to about 34 Watt/Kg. As will be understood by one of ordinary skill in the art, these are measures of mixing energy.

The means for subjecting the components to the mixing energy may be selected from a variety of well-known apparatuses (energizing means). For example, this energizing means may be a mixer which provides energy to the liquid medium by forming ultrasonic vibrations therein, e.g., a Sonolator, commercially available from Sonic Corporation, Stratford, Conn. or Piezoelectric transducers. The Sonolator is an in-line system providing ultrasonic vibrations by pumping a liquid, a blend of liquids, or a solid dispersion in a liquid through a shaped orifice at a high linear velocity. The liquid stream impinges against a blade cantilevered in the stream. Flow over the blade causes vibrations in the blade that produces cavitation in the stream converting flow energy into mixing/dispersion energy. Other particularly useful energizing means include batch mixers providing a high agitator tip speed, e.g., blenders as available from Sunbeam Corporation of Delray Beach, Fla. with the brand name OSTERIZER. Additionally rotor/stator high shear mixers, commercially available from Charles Ross & Son, Hauppauge, N.Y. may be useful. In-line mixers such as are available from Quadro Inc., Millburn, N.J., as model Quadro ZC/XC are useful as well. Additionally, particularly preferred energizing means for use herein include bottom-driven mixtures such as the Breddo Likwifier (Model LOR, round tank; Model LTD square tank) commercially available from Breddo Likwifier, Kansas City, Mo. and APV Mixer/Blender (Multiverter (round tank)/Liquiverter (square tank) high speed mixers commercially available from APV Crepaco, Inc., Lake Mills, Wis.

With respect to the processes of the present invention, the protein component is combined with the lipid component to form a protein/lipid mixture. Preferably, the protein component is combined with an aqueous liquid (for example, water) and subjected to high shear conditions prior to combination with the lipid component. Wherein the protein component is combined with such aqueous liquid, the resulting mixture is preferably subjected to such high shear conditions for from about 2 minutes to about 20 minutes, more preferably from about 5 minutes to about 15 minutes, all depending upon the desired batch size.

The protein/lipid mixture is subjected to high shear conditions, homogenization, or a combination thereof, preferably a combination thereof. Preferably, the protein/lipid mixture is subjected to such high shear conditions for from about 2 minutes to about 20 minutes, more preferably from about 5 minutes to about 15 minutes, all depending upon the desired batch size. The protein/lipid mixture may then be homogenized at a pressure of from about 1,000 psi to about 15,000 psi to form a homogenized protein/lipid mixture. Preferably, the protein/lipid mixture is homogenized at a pressure of from about 2,000 psi to about 10,000 psi, more preferably from about 3,000 psi to about 7,000 psi.

Preparation of the protein/lipid mixture may be done at a variety of temperatures. Preferably, such preparation is conducted at a temperature of from about 4° C. to about 88° C., more preferably from about 4° C. to about 30° C., even more preferably from about 10° C. to about 22° C., and most preferably from about 14° C. to about 22° C. Means of temperature control are commonly known in the art.

Preferably, the high shear conditions and/or homogenization of the protein/lipid mixture results in the lipid component having the median particle sizes described herein.

In a preferred embodiment of the present processes, the prepared composition comprises a mineral salt and/or an emulsifier, as described herein. Indeed, the present inventors have discovered that particularly useful processes herein involve combination of such mineral and/or emulsifier subsequent to preparation of the protein/lipid mixture. This order of addition has been found to be particularly important. For example, the homogenization pressures used to prepare the protein/lipid mixture have been found to disrupt the vesicle components. Accordingly, by first homogenizing the protein/lipid mixture, followed by combination with the vesicle components, compositions may be provided wherein the protein/lipid mixture is stabilized without compromising the integrity of the vesicle components.

Therefore, in a preferred step of the present processes, the process further comprises combining and mixing the homogenized protein/lipid mixture with a vesicle component comprising the mineral and the emulsifier to form a protein/lipid/vesicle mixture. This mixing is typically performed under conditions of low shear (e.g., less than about 3,500 RPM (for example, using a rotor-stator mixer), preferably less than about 500 RPM (for example, using a Hydro-foil A3 impeller or Pitch Blade impeller), even more preferably less than about 250 RPM, and most preferably less than about 100 RPM, alternatively or additionally a NP/M of about 1 Watt/Kg or less) to assist with preservation of the vesicle component. The mixing may be performed at a variety of temperatures. Preferably, in order to ensure that the emulsifier remains pliable or in a liquid state during mixture, such mixing is preferably performed at a temperature of from about 4° C. to about 100° C., more preferably from about 70° C. to about 93° C., and most preferably from about 74° C. to about 85° C. Optionally, the protein/lipid mixture and vesicle components may be each, individually, at a temperature in these ranges prior to combination and mixing.

In yet another preferred embodiment of the present invention, the inventive processes further comprise combining the protein/lipid/vesicle mixture with a second mixture comprising a protein component and a lipid component, to form a second protein/lipid/vesicle mixture. The second mixture may have the same composition as the protein/lipid mixture, or may be of different composition. Preferably, the second mixture has the same composition as the protein/lipid mixture. The second composition may be prepared in the same manner described herein above for the protein/lipid mixture.

Once mixed, the protein/lipid/vesicle mixture (or the second protein/lipid/vesicle mixture, if applicable) may be cooled and subjected to, for example, any pH adjustments, further ingredient additions, or conditions such as sterilization. Preferably, the protein/lipid/vesicle mixture or the second protein/lipid/vesicle mixture is homogenized at a pressure of from about 500 psi to about 1,500 psi, more preferably from about 800 psi to about 1,200 psi.

EXAMPLES

The following are non-limiting examples of the present compositions. The compositions are preferably prepared using the inventive process described herein. The following examples are provided to illustrate the invention and are not intended to limit the scope thereof in any manner.

Example 1

A mocha-flavored beverage composition is prepared having the following components in approximately the indicated amounts:

| Component | Weight Percent |
| --- | --- |
| Gums | 0.01 |
| Nutrients, including ferrous fumarate | 0.58 |
| Soy Lecithin | 0.02 |

-continued

| Component | Weight Percent |
|---|---|
| Ethyl Oleate | 1.04 |
| Fluid Milk | 48.61 |
| Sugar | 1.98 |
| Flavoring Agents, including coffee, chocolate syrup, vanilla powder | 12.47 |
| Emulsifier | 0.46 |
| Water | Quantum satis |

Example 2

A mocha-flavored beverage containing fiber composition is prepared having the following components in approximately the indicated amounts:

| Component | Weight Percent |
|---|---|
| Gums | 0.01 |
| Nutrients, including ferrous fumarate | 0.58 |
| Soy Lecithin | 0.02 |
| Ethyl Oleate | 1.04 |
| Fluid Milk | 48.61 |
| Sugar | 1.98 |
| Flavoring Agents, including coffee, chocolate syrup, vanilla powder | 12.47 |
| Emulsifier | 0.46 |
| Arabinogalactan | 2.3 |
| Water | Quantum satis |

What is claimed is:

1. A composition comprising:
   (a) a protein component comprising a protein selected from the group consisting of whey, casein, and mixtures thereof;
   (b) a lipid component comprising a fatty acid material selected from the group consisting of fatty acids, non-glyceryl esters of the fatty acids, and mixtures thereof, wherein the lipid component has a median particle size of less than about 1 micron; and
   (c) from about 0.01% to about 0.5% by weight of the composition of an emulsifer which is additional to the lipid component and the protein component and which is selected from the group consisting of phospholipids, glycolipids, and mixtures thereof; and
   (d) a vesicle component comprising the emulsifier and a mineral.

2. The composition according to claim 1 wherein the median particle size of the lipid component is from about 0.4 microns to about 0.8 microns.

3. The composition according to claim 2 wherein the fatty acid material is selected from the group consisting of lauric acid, lauroleic acid, myristic acid, myristoleic acid, pentadecanoic acid, palmitic acid, palmitoleic acid, margaric acid, stearic acid, dihydroxystearic acid, oleic acid, ricinoleic acid, elaidic acid, linoleic acid, alpha-linolenic acid, dihomogamma-linolenic acid, eleostearic acid, licanic acid, arachidonic acid, arachidic acid, eicosenoic acid, eicosapentaenoic acid, behenic acid, erucic acid, docosahexaenoic acid, lignoceric acid, non-glyceryl esters of the fatty acid material, and mixtures thereof.

4. The composition according to claim 1 wherein the mineral is selected from the group consisting of iron, calcium, zinc, copper, magnesium, manganese, and mixtures thereof.

5. The composition according to claim 4 wherein the mineral is a divalent salt having the formula:

MA wherein M is a divalent metal selected from the group consisting of iron, calcium, zinc, copper, magnesium, manganese, and mixtures thereof, and wherein A is a dicarboxylate anion.

6. The composition according to claim 1 wherein the emulsifier is selected from the group consisting of lecithins, cephalins, plasmalogens, and mixtures thereof.

7. The composition according to claim 6 wherein the protein component is dry milk and wherein the composition comprises from about 0.5% to about 5% of the dry milk, by weight of the composition.

8. The composition according to claim 7 wherein the fatty acid material is selected from the group consisting of oleic acid, linoleic acid, non-glyceryl esters thereof, and mixtures thereof.

* * * * *

UNITED STATES PATENT AND TRADEMARK OFFICE
CERTIFICATE OF CORRECTION

| | |
|---|---|
| PATENT NO. | : 7,393,552 B2 |
| APPLICATION NO. | : 10/357636 |
| DATED | : July 1, 2008 |
| INVENTOR(S) | : Leonard E. Small et al. |

It is certified that error appears in the above-identified patent and that said Letters Patent is hereby corrected as shown below:

<u>Section 4</u>

<u>Line 55</u> – Please delete "or branched (for example, which form" and insert -- or branched (for example, *iso*-propyl) chain. Highly preferred ester chains include those which form --.

<u>Section 13</u>

<u>Line 28</u> – Please delete "oligosaccharides com linked to a molecule of sucrose. Most" and insert -- ogligosaccharides composed of a chain of fructose molecules linked to a molecule of sucrose. Most --.

Signed and Sealed this

Ninth Day of June, 2009

JOHN DOLL
*Acting Director of the United States Patent and Trademark Office*